(12) United States Patent
Donaldson et al.

(10) Patent No.: US 8,211,025 B2
(45) Date of Patent: Jul. 3, 2012

(54) FOUR-WAY STEERABLE CATHETER SYSTEM AND METHOD OF USE

(75) Inventors: Brenda L. Donaldson, Harrison Township, MI (US); Douglas G. Wildes, Ballston Lake, NY (US); Paul Martin Backer, Winsted, MN (US); Marc Donald Knutson, Zimmerman, MN (US)

(73) Assignee: General Electric Company, Schenectady, NY (US)

( * ) Notice: Subject to any disclaimer, the term of this patent is extended or adjusted under 35 U.S.C. 154(b) by 1104 days.

(21) Appl. No.: 11/677,791

(22) Filed: Feb. 22, 2007

(65) Prior Publication Data
US 2008/0097403 A1 Apr. 24, 2008

Related U.S. Application Data

(60) Provisional application No. 60/862,367, filed on Oct. 20, 2006.

(51) Int. Cl.
*A61B 8/14* (2006.01)
(52) U.S. Cl. .................. 600/459; 604/95.04
(58) Field of Classification Search .......... 604/95.01, 604/95.04, 528, 96.01, 99.01; 600/585, 146–147, 600/407, 437, 459
See application file for complete search history.

(56) References Cited

U.S. PATENT DOCUMENTS

| | | | | |
|---|---|---|---|---|
| 4,332,254 A | * | 6/1982 | Lundquist | 606/194 |
| 4,375,818 A | * | 3/1983 | Suwaki et al. | 600/463 |
| 4,723,936 A | | 2/1988 | Buchbinder et al. | |
| 5,176,141 A | * | 1/1993 | Bom et al. | 600/467 |
| 5,662,116 A | * | 9/1997 | Kondo et al. | 600/462 |
| 5,938,616 A | * | 8/1999 | Eaton et al. | 600/463 |
| 6,120,453 A | * | 9/2000 | Sharp | 600/463 |
| 6,464,645 B1 | * | 10/2002 | Park et al. | 600/462 |
| 7,798,971 B2 | * | 9/2010 | Flesch et al. | 600/459 |

* cited by examiner

*Primary Examiner* — Theodore Stigell
(74) *Attorney, Agent, or Firm* — McAndrews, Held & Malloy, Ltd.; David Bates; Jacob Groethe

(57) ABSTRACT

Certain embodiments provide systems and methods for catheter positioning. Certain embodiments provide a catheter for use in at least intravenous and intracardiac spaces. The catheter includes a catheter body having a length and a tip portion at a distal end of the catheter body. The catheter also includes a plurality of wires for moving the catheter body in a plurality of directions. The catheter further includes a first control for manipulating the plurality of wires in two primary planes of movement for the catheter body. The catheter includes a second control for manipulating the plurality of wires in two secondary planes of movement for the catheter body. The second control is distinct in appearance and operation from the first control.

15 Claims, 5 Drawing Sheets

Prior Art

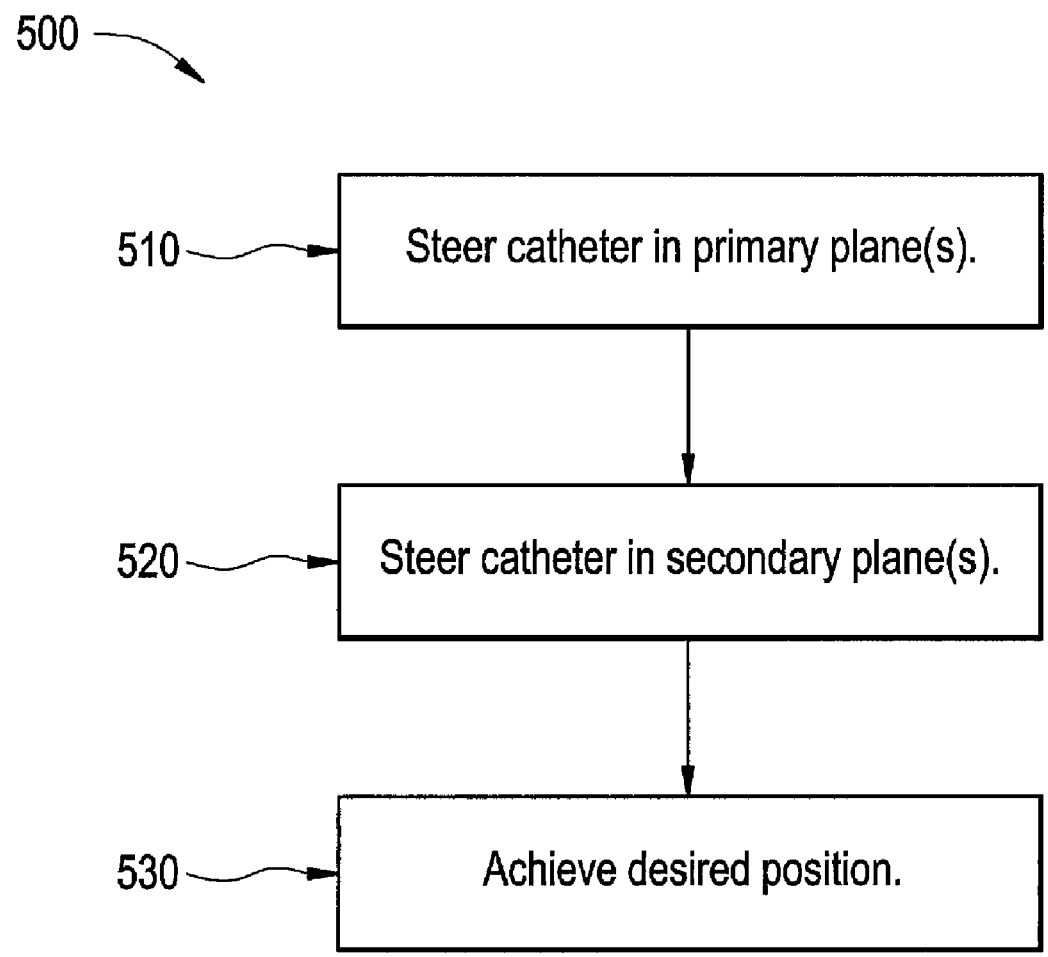

FOUR-WAY STEERABLE CATHETER SYSTEM AND METHOD OF USE

CROSS-REFERENCE TO RELATED APPLICATIONS

This application claims priority to a provisional application entitled "Four-Way Steerable Catheter System and Method of Use," filed on Oct. 20, 2006, as Ser. No. 60/862,367, which is herein incorporated by reference in its entirety.

BACKGROUND OF THE INVENTION

The present invention generally relates to catheter systems. More specifically, certain embodiments of the present invention related to four-way steerable catheter systems.

Current catheter systems with movable guide wires present disadvantages such as limited steerability, which is currently dependent upon the torque control of the movable wire. Steerability is highly significant in a cardiovascular procedure, such as percutaneous transluminal coronary angioplasty (PTCA), or angioplasty, because less steerability results in greater time spent in the body and more possible patient trauma. Multiple insertions of guide wires and catheters can lead to thrombosis because, for example, coagulation may commence along a guide wire surface and be forced into the heart when a catheter is slid over the guide wire. Furthermore, there are some blockages which cannot be reached with presently known equipment.

As procedures become more and more complex, physicians have a need to pinpoint exact physical locations inside the body particularly the heart. The currently available catheters are 2-way deflectable, meaning the doctor finds an area fairly close to what he wants to view and then torques the catheter to try to maintain the correct field of view. Currently physicians have resorted to using sterile tape to try to hold the handle and the shaft in an exact location. This can be quite problematic when the patient moves his or her legs, as the entire ultrasound system then gets moved away from the area of interest. In some teaching hospitals, a resident must stand at the patient's bedside holding the catheter to assure good visualization through the procedure. This exposes the resident to radiation that he/she would not normally be required to absorb. Traditionally 1 or 2 pull wires are placed in a catheter allowing the intracardiac echocardiography (ICE) or intravascular ultrasound (IVUS) catheter to bend either one direction or 2 directions. An example of one able to move both ways is shown in FIG. 1.

Thus, there is a need for catheter systems and methods for improved positioning of a catheter. There is also a need for systems and methods providing improved control of a catheter.

BRIEF SUMMARY OF THE INVENTION

Certain embodiments provide systems and methods for catheter positioning. Certain embodiments provide a catheter for use in at least intravenous and intracardiac spaces. The catheter includes a catheter body having a length and a tip portion at a distal end of the catheter body. The catheter also includes a plurality of wires for moving the catheter body in a plurality of directions. The catheter further includes a first control for manipulating the plurality of wires in two primary directions of movement for the catheter body. The catheter includes a second control for manipulating the plurality of wires in two secondary directions of movement for the catheter body. The second control is distinct in appearance and operation from the first control.

Certain embodiments provide a method for positioning a catheter. The method includes steering a catheter tip in a first direction using a first wire, steering the catheter tip in a second direction using a second wire, and achieving a desired position for use of the catheter tip using at least two controls. Each of the at least two controls controls a subset of the wires, and each of the at least two controls is distinct in appearance and operation from each other of the at least two controls.

Certain embodiments provide a catheter tip control system. The system includes a catheter tip including a transducer array for at least one of two-dimension, three-dimensional and four-dimensional imaging. The system further includes four steering wires for manipulating the catheter tip. Each of the four steering wires is capable of moving the catheter tip in a certain direction. The four steering wires are capable of manipulating the catheter tip to achieve a desired position. The system also includes first and second controls for manipulating the four steering wires to achieve the desired position. The first and second controls are used differently to manipulate the steering wires.

BRIEF DESCRIPTION OF SEVERAL VIEWS OF THE DRAWINGS

FIG. 5 illustrates a flow diagram for a method for positioning a catheter in accordance with an embodiment of the present invention.

Figure 1:
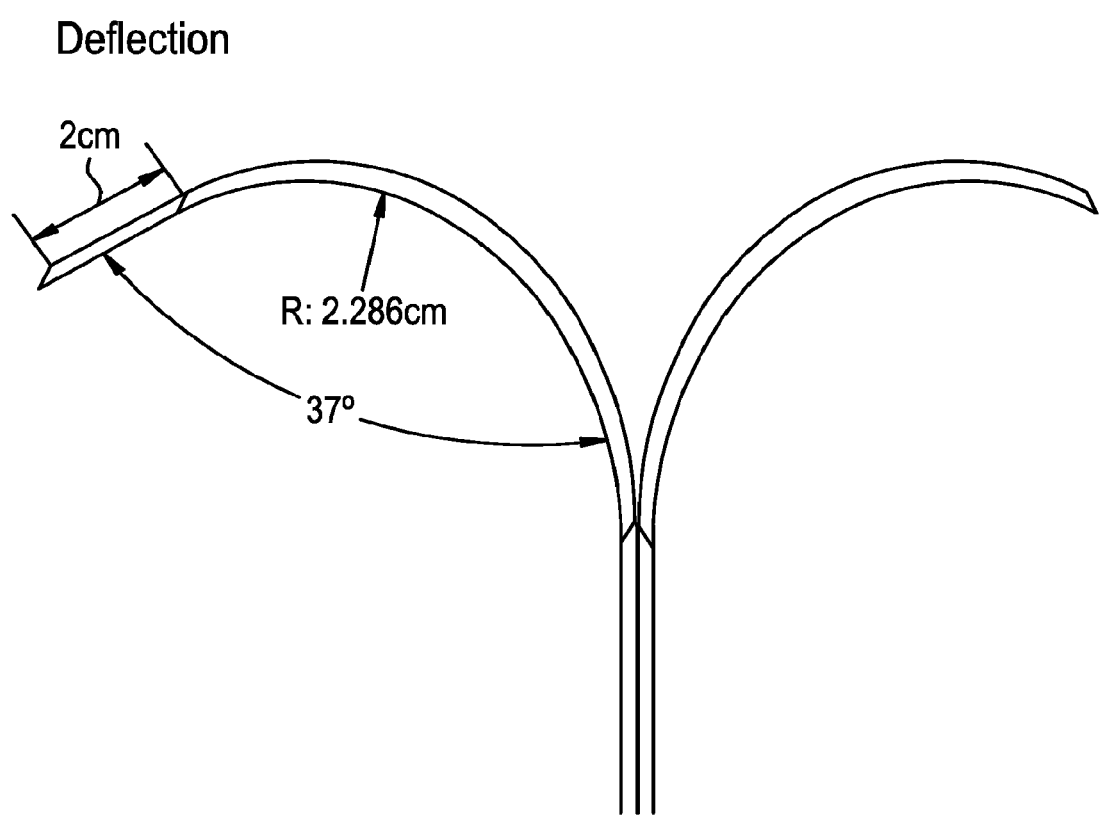
FIG. 1 illustrates a two-wire, two-direction catheter.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 2:
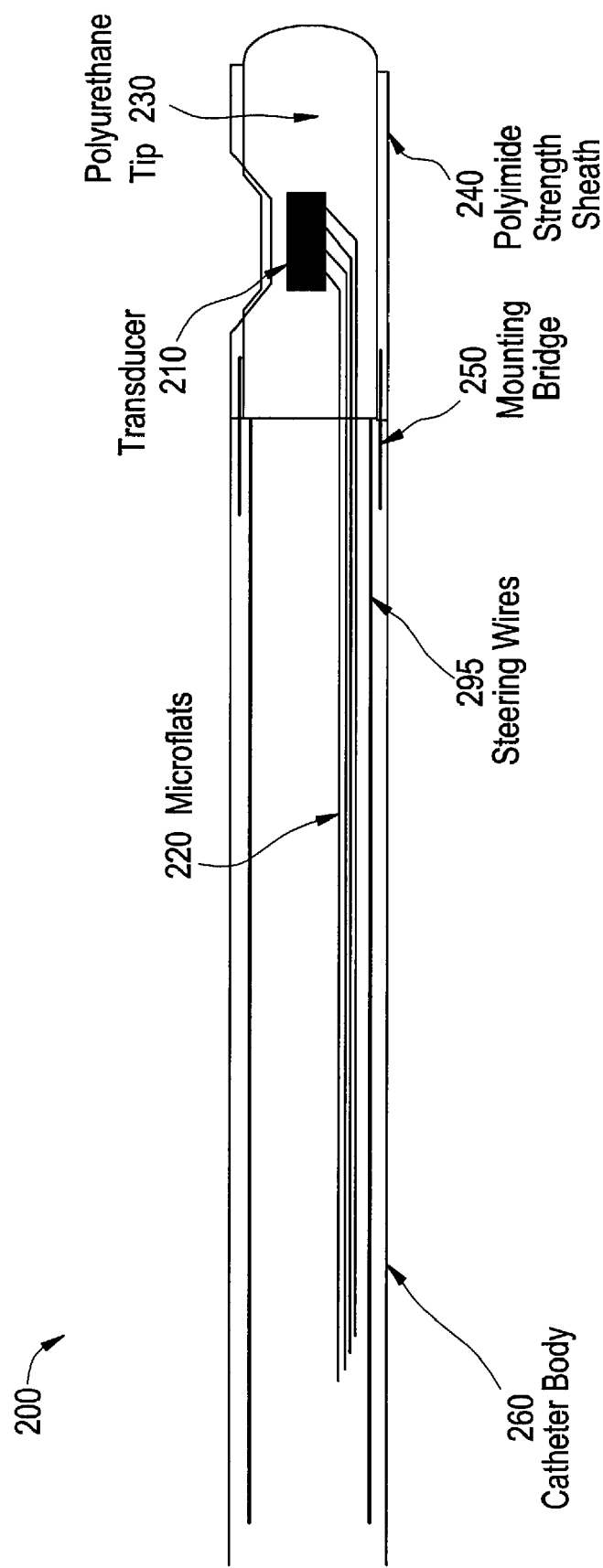
FIG. 2 illustrates a cross-sectional view of a catheter system for two-dimensional imaging in accordance with an embodiment of the present invention.

FIG. 2 illustrates a cross-sectional view of a catheter system 200 for two-dimensional (2D) imaging in accordance with an embodiment of the present invention. The catheter 200 is described, for purposes of illustration only, as an intracardiac echocardiography (ICE) catheter but may also be implemented with other applications, such as transesophageal probes or endoscopes and/or intravascular ultrasound (IVUS) catheters. The presently described technology may also be placed in cryoablation catheters. The presently described technology may be used in 2D, three dimensional (3D) and/or four-dimensional (4D) catheter systems and applications. Catheters are also used in other parts of the body, for instance to close off connections between an artery and a vein anywhere in the body. An ability to move in more than a single plane may help to provide an ability to treat areas which otherwise could not be reached.

The 2D catheter system 200 includes a transducer 210, transducer wiring 220, a tip 230, a tip support tube 240, a bridge 250, a catheter body 260, a catheter handle 270 (not pictured), a catheter connector tubing 280 (not pictured) and a catheter connector 290 (not pictured). A plurality of steering wires 295 may be used to steer and position the catheter 200 in a plurality of directions.

The tip 230 of the 2D catheter system 200 can be produced, for example, by molding the transducer 210 into a soft polyurethane material. This produces a tip 230 that resembles a bullet with a flattened side that is used as the transducer window. A polyimide tip support tube 240 is slid over the polyurethane tip 230 in order to give the tip 230 some rigidity, for example. A round hollow bridge tube 250 is slid over the end of the proximal end of the bullet tip 230 and attached to the tip 230. The transducer wires 220 are pulled through the catheter body 260, through the catheter handle 270 and through the catheter connector tubing 280, for example. The other end of the round hollow bridge tube 250 slides into the catheter body 260 and attaches to the catheter body 260. This hollow bridge 250 connects the catheter tip 230 to the catheter body 260. The transducer wires 220 are then connected to a printed circuit board in the connector 290. The printed circuit board is then placed in the connector 290 and screwed together or otherwise attached to clamp the connector 290 onto the catheter connector tubing 280.

Figure 3:
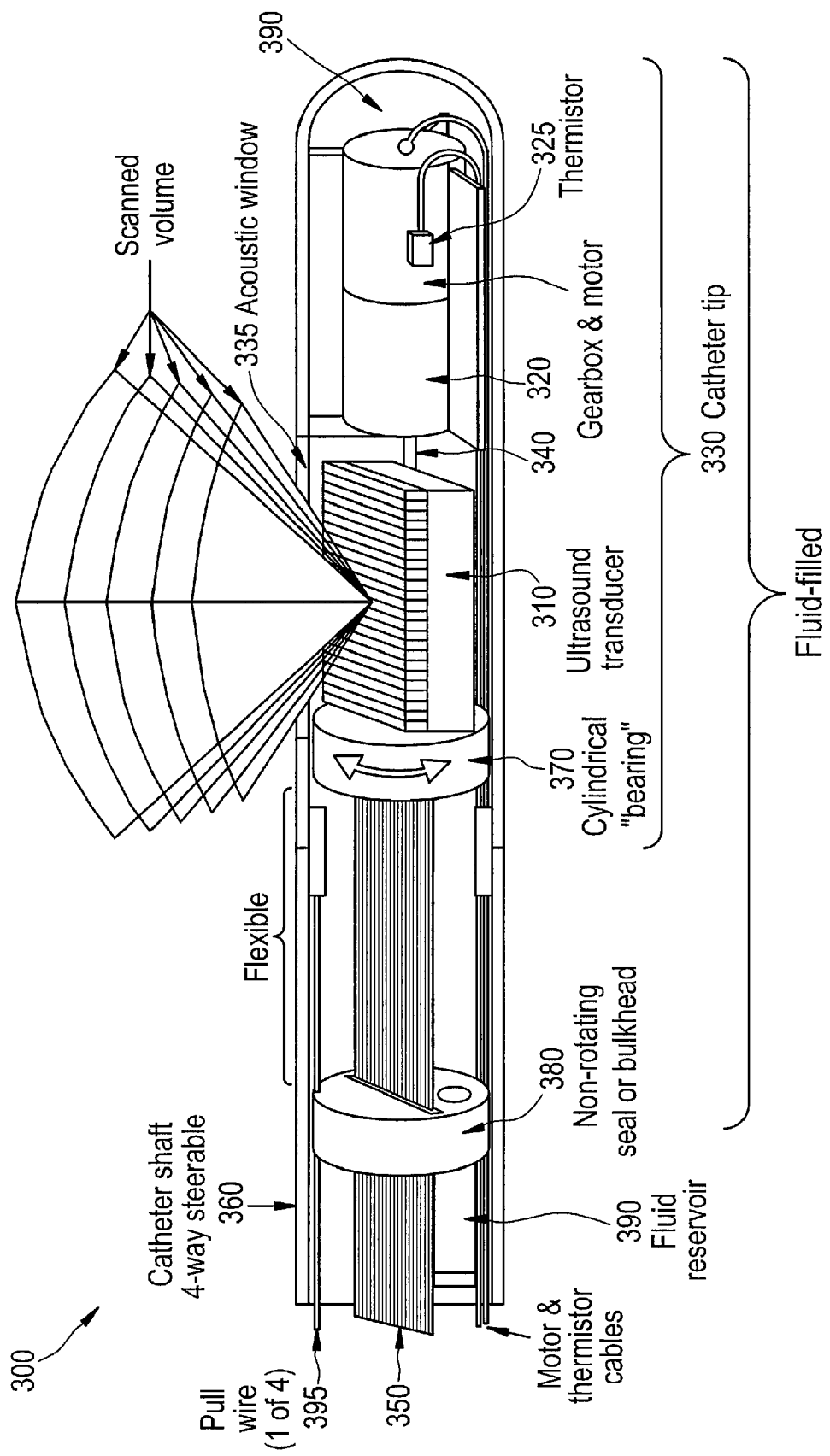
FIG. 3 illustrates a catheter system for four-dimensional imaging in accordance with an embodiment of the present invention.
Figure 4A:
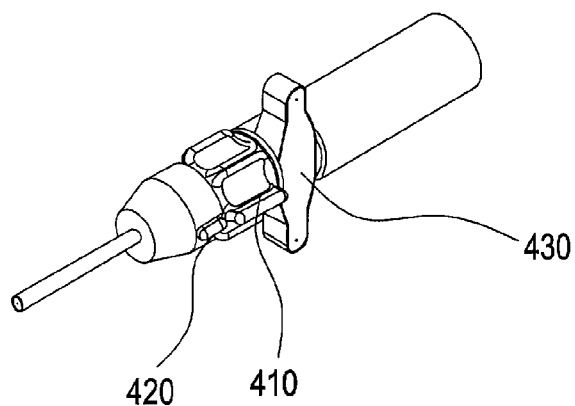
FIG. 4 illustrates a plurality of exemplary control implementations in a catheter system in accordance with an embodiment of the present invention.
Figure 4B:
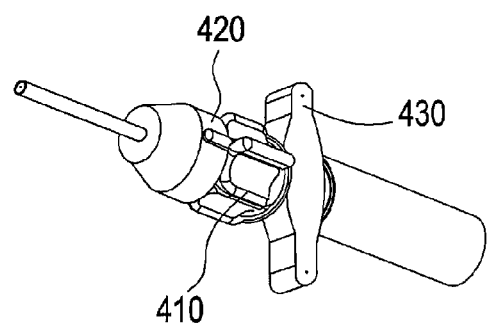
Figure 4C:
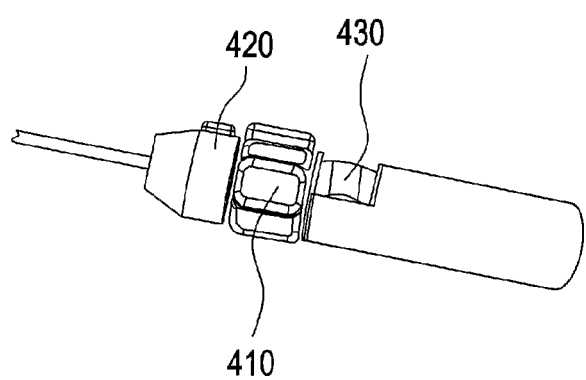
Figure 4D:
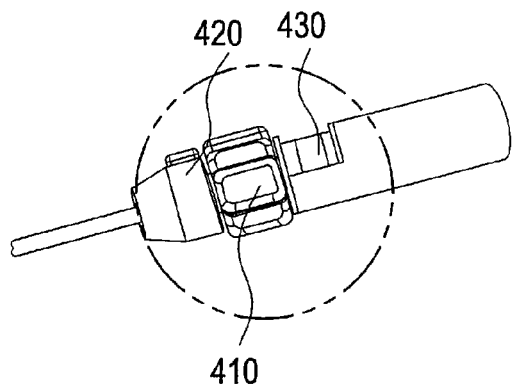

FIG. 3 illustrates a 4D catheter system 300 in accordance with an embodiment of the present invention. The catheter 300 is described, for purposes of illustration only, as an ICE catheter but may also be implemented with other applications, such as transesophageal probes or endoscopes and/or IVUS catheters. The presently described technology may also be placed in cryoablation catheters. The presently described technology may be used in 2D, three dimensional (3D) and/or four-dimensional (4D) catheter systems and applications. Catheters are also used in other parts of the body, for instance to close off connections between an artery and a vein anywhere in the body, the ability to move in more than a single plane could provide the ability to treat areas which otherwise could not be reached.

The 4D catheter system 300 includes a transducer array 310, a motor and gearbox 320, a tip section 330, a coupling or drive shaft 340, a connection cable 350 and a catheter body 360. The system 300 also includes a bearing 370, a bulkhead 380, a fluid reservoir 390 and a plurality of steering wires 395. In certain embodiments, the system 300 may also include a thermistor 325.

In certain embodiments, the transducer array 310 is a one-dimensional (1D) array. The 1D transducer array 310 of the 4D catheter system 300 is a rotatable array. For example, the 4D catheter system 300 has a transducer array 310 capable of rotating plus or minus 30° at 7 volumes/second in a 10 French steerable catheter. A motor and gearbox 320 are also included in the transducer tip section 330, and are located distal to the transducer array 310 in the tip section 330. A coupling or drive shaft 340 is positioned between the motor and gearbox 320 and the transducer array 310 in the tip section 330. A flexible cable 350 for electrical connections to the transducer 310 extends through the tip section 330 and into the catheter body 360.

In certain embodiments, the transducer array 310 is arranged for oscillatory rotation around the catheter axis (i.e., back and forth, rather than continuously around). In certain embodiments, the transducer array 310 and motor 320 are controlled using an open-loop control. However, a transducer rotation angle sensor may be used for motion feedback. The motor drive electronics and motion control system are located outside the catheter 300, such as in an additional "pod" or in an ultrasound system.

An acoustic coupling fluid is introduced between the oscillating transducer 310 and surrounding tip section 330. The transducer array 310 is positioned in the tip section 330 in an acoustic window 335, which allows an ultrasound beam to pass through with minimum impact on beam and image. The acoustic window 335 may be formed of polyurethane or polymethylpentene, for example.

The transducer 310 may have a "lens" of some sort to minimize an effect of coupling fluid and tip section material on an ultrasound beam. The tip section 330 may include a fluid reservoir 390 to accommodate thermal expansion and to compensate for fluid loss during catheter system storage. The tip section 330 and fluid reservoir 390 are sealed to isolate the tip section 330 from the catheter body 360.

In certain embodiments, one or more hard stops are placed in the tip section 330 to limit rotation (i.e., prevent 360° rotation) and initialize alignment of the transducer 310, acoustic window 335, and motor controller. A "bearing" 370 is used to align the oscillating transducer 310 within the 4D tip 330 and/or minimize friction between the transducer 310 and surrounding tip section 330, for example. The bearing 370 may be as simple as three or more contact points, for example. A bulkhead 380 separates the 4D tip section 330 from the catheter body 360 and also separates rotating versus non-rotating sections of cable 350. The bulkhead 380 helps join the tip section 330 to the catheter body 360 and provides a fluid seal to keep acoustic coupling fluid in the tip section 330 and out of the catheter body 360. The tip section 330 may be a plastic tube, or may comprise both plastic (e.g., for an acoustic window, biocompatible surface) and metal (e.g., for stiffness, reliability, dimensional control), for example.

In certain embodiments, the catheter body is a four-way steerable catheter body with a diameter of between 9 and 10 French (~3 πmm), and a tip section after the catheter body includes a transducer array inside the tip section. The transducer array can be a one dimensional phased array of 64 elements with a pitch of 0.110 nm, for example. In certain embodiments, the transducer array operates a center frequency of approximately 6.5 MHz.

The transducer array may be mounted inside a tube-shaped tip that is mounted on the end of the catheter. In certain embodiments, the array is not mounted on the outside surface of the catheter or on the outside surface of the tip as this would increase the diameter of the catheter/tip combination and prevent 2D and 4D ICE catheter systems from being used in some veins and areas of a patient's anatomy. The tip includes an acoustic window that permits ultrasound beams transmitted by the array to pass through the tip. The acoustic window can be formed of polyurethane, for example. This acoustic window may also act as a lens to focus the ultrasound beams to a focal point in a patient's anatomy.

In certain embodiments, the transducer array elements are formed of a piezoelectric material. The tip attached to the end of the catheter may be formed of a combination of materials to help ensure that the tip is a rigid, non-flexible body. For example, the tip may be primarily formed of polyurethane that is surrounded by a polyimide "jacket" that provides the stiffness and rigidity desired for the tip. The tip may be a rigid, non-flexible body to help ensure that the tip cannot be bent so as to damage the transducer array enclosed therein.

In certain embodiments, the 2D and 4D catheter systems are capable of all standard ultrasound cardiology imaging modes, including B-mode, color doppler, pulsed-wave (PW) doppler, and continuous-wave (CW) Doppler. The catheter systems facilitate contrast imaging. The 2D and 4D catheter systems may also include additional components, such as a thermistor (i.e., a thermally sensitive resistor used for temperature measurement and control, etc.).

In certain embodiments, incorporation of four steering wires into a catheter allows a clinician to set the catheter to a desired location/position/configuration. In certain embodiments, a user may then lock the catheter at that location/position/configuration. Several handle types and curve configurations may be implemented using such a multiple pull wire system. In certain embodiments, a single control or handle is used to control the plurality of steering wires. In other embodiments, steering pull wires may be divided into subsets and a control or handle may be used to control a subset of wires. In certain embodiments, other mechanisms, such as springs, strings, cables, fiber bundles and/or other thin, flexible tension members may be used to position a catheter. For simplicity, such mechanisms are collectively referred to as steering wires herein.

In certain embodiments, primary movement is performed in one plane, while an orthogonal plane is not likely to have much movement (e.g., not likely to be more than 20 degrees). One handle or control may be configured to control the main movement of the catheter. Movement in the other plane may be controlled by a smaller and more discrete control, for example. One or more controls may include a marker or other indication of wire position midpoint. In certain embodiments, a control can be held in one place without the user's hand applied to the handle. In certain embodiments, a control can be held in one place with minimal pressure applied by the user, for example.

In certain embodiments, steering wires and one or more controls are implemented with a catheter capable of producing real time 3D images with additional catheter tip components and moving parts. In certain embodiments, a primary control or handle may be designed so that the major movement of the catheter is controlled with wing type controls and/or with a rotating, variegated or other dial, for example. A secondary control (for example, one facilitating less movement and/or movement in one or more different planes) can be implemented either by a variegated, rotating or other dial, by a small slide bar, and/or any combination thereof, for example.

FIG. 4 illustrates a plurality of exemplary control implementations in a catheter system in accordance with an embodiment of the present invention. The examples of FIG. 4 are presented for purposes of illustration only. FIGS. 4A, 4B, 4C and 4D illustrate catheters with a variegated dial 410, a midpoint indicator 420 and a wing control 430. The variegated dial 410 controls secondary planes of movement. The wing control 430 controls primary planes of movement. The midpoint indicator 420 provides a visual indication of the midpoint in the secondary and/or primary planes of movement. In certain embodiments, the dial 410 may be used to control primary planes of movement while the wing control 430 controls secondary planes of movement.

In certain embodiments, the catheter may include a locking mechanism to lock or maintain a catheter position. For example, once a user has manipulated one or more controls 410, 430, a locking mechanism may be used to hold the position of the catheter for use by the user. Alternatively and/or in addition, resistance (e.g., friction, etc.) and/or tension may be provided to help maintain a desired curvature, angle and/or other position of a catheter during use. In certain embodiments, a lock, tension and/or resistance may be used to maintain a control or dial in a certain position (e.g., at a midpoint or other desired position) without pressure by a user, for example. In certain embodiments, a control may be used to apply a certain amount of tension or friction to help maintain a catheter position/orientation, for example.

One or more controls 410, 430 used in conjunction with steering wires, cords, springs, etc., may facilitate manipulation of the catheter. In certain embodiments, one or more controls 410, 430 may be used with steering wires, cords, springs, strings, cables, fiber bundles, etc., for rotation and/or deflection (e.g., bending) of the catheter. For example, one or more controls 410, 430 may pull a steering wire or cord, apply tension to a spring, etc. to move the catheter. Pushing and/or pulling of a control 410, 430, for example, may cause a distal end of the catheter to deflect from one or more planar axes, for example. Rotation of a control 410, 430, for example, may result in rotation of the catheter tip to a desired orientation.

In certain embodiments, one or more controls 410, 430 may also be used to inflate a balloon at a distal end of the catheter, ablate tissue, deliver a substance, guidewire and/or instrument at the distal end of the catheter, etc.

FIG. 5 illustrates a flow diagram for a method 500 for positioning a catheter in accordance with an embodiment of the present invention. At step 510, a catheter tip is steered in one or more primary planes of movement. For example, a wing control may be used in conjunction with one or more steering wires to manipulate the catheter tip with respect to one or more primary planes of movement.

At step 520, the catheter tip is steered in one or more secondary planes of movement. For example, a slide bar control may be used in conjunction with one or more steering wires to manipulate the catheter tip with respect to one or more primary planes and/or directions of movement. In certain embodiments, step 520, movement in one or more secondary planes and/or direction, may not occur as often as movement in primary plane(s). Alternatively and/or in addition, movement in one or more secondary planes may be smaller than movement in one or more primary planes. In certain embodiments, movement in both primary and secondary plane(s) and/or direction(s) may be controlled using a single control (e.g., wing, bar, dial, etc.), for example.

At step 530, a desired position is achieved for use of said catheter. That is, after the catheter tip is steered or manipulating using one or more wires, a desired position is achieved so that the catheter may be used by a clinician.

In certain embodiments, four wires are used to steer the catheter using one or more controls to position the catheter at a desired position (e.g., rotation, deflection, etc.). For example, two or more controls may be used to manipulate the catheter tip using the first, second, third and fourth wires. In certain embodiments, more than four wires may be used and/or wires may be combined to maneuver in multiple planes/directions, for example. In certain embodiments, a transducer array is rotated within the catheter tip to obtain at least one 2D, 3D and/or 4D image. In certain embodiments, a guidewire, instrument and/or substance, for example, may be delivered into a body via the catheter and control(s).

Thus, certain embodiments allow catheter access and positioning for visualization and possible intervention at locations within the body which currently either cannot be maintained or require added personnel to achieve the catheter placement. By maintaining catheter position, procedure times can be shortened and procedures can be done that may not otherwise be completed without the necessary visualization.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A catheter comprising:
    a catheter body located at a proximal end of said catheter;
    a tip portion located at a distal end of said catheter;
    an ultrasound transducer array located in the tip portion;
    a flexible cable configured to provide electrical connections to said ultrasound transducer, said flexible cable extending from said ultrasound transducer in said tip portion into said catheter body, wherein said flexible cable comprises a rotating section and a non-rotating section;
    a motor located in the tip portion and configured to rotate said ultrasound transducer array around an axis of said catheter using a drive shaft;
    a cylindrical bearing located in the tip portion configured to at least one of align the ultrasound transducer array within the tip portion and reduce friction between the ultrasound transducer array and the tip portion;
    a bulkhead configured to separate said tip portion from said catheter body and configured to separate said rotating section of said flexible cable and said non-rotating section of said flexible cable;
    a plurality of wires configured to move said tip portion in a plurality of directions;
    a first control configured to manipulate said plurality of wires in two primary directions of movement for said tip portion; and
    a second control configured to manipulate said plurality of wires in two secondary directions of movement for said tip portion.

2. The catheter of claim 1, wherein said plurality of wires comprises four wires configured to move said tip portion in four directions.

3. The catheter of claim 1, wherein said plurality of wires are configured to pull said tip portion and to move said tip portion in a plurality of directions.

4. The catheter of claim 1, further comprising a position marker configured to indicate a midpoint of at least one plane of movement of said tip portion.

5. The catheter of claim 1, wherein said first control comprises a wing control and said second control comprises a dial control.

6. The catheter of claim 1, wherein said catheter is configured for use at in four-dimensional imaging.

7. The catheter of claim 1, wherein at least a portion of the wires terminates before the tip portion.

8. The catheter of claim 1, further comprising a third control configured to cause a balloon to be inflated.

9. The catheter of claim 1, further comprising a third control configured to cause a tissue to be ablated.

10. The catheter of claim 1, further comprising a third control configured to cause a substance to be delivered into a patient.

11. The catheter of claim 1, further comprising a third control configured to cause a guidewire to be delivered into a patient.

12. The catheter of claim 1, further comprising a third control configured to cause an instrument to be delivered into a patient.

13. The catheter of claim 1, wherein at least one of said first control and said second control comprises a slide bar control.

14. The catheter of claim 1, wherein the first control and the second control are part of a single control.

15. The catheter of claim 1, wherein said bulkhead provides a fluid seal configured to prevent acoustic coupling fluid in said tip portion from entering said catheter body.

* * * * *